United States Patent [19]

Krueger et al.

[11] Patent Number: 5,144,958
[45] Date of Patent: Sep. 8, 1992

[54] APPARATUS FOR CONDUCTING MAMMALIAN DERMATOLOGICAL STUDIES

[75] Inventors: Andrew J. Krueger, Levittown, Pa.; Joseph J. Yang, Warren, N.J.

[73] Assignee: Mobil Oil Corporation, Fairax, Va.

[21] Appl. No.: 570,752

[22] Filed: Aug. 22, 1990

Related U.S. Application Data

[62] Division of Ser. No. 372,489, Jun. 28, 1989, Pat. No. 4,971,066.

[51] Int. Cl.$^5$ .............................................. A61B 5/00
[52] U.S. Cl. .................................. 128/743; 128/888; 604/304
[58] Field of Search ................. 128/630, 743, 887–888, 128/632, 760; 604/289, 304, 307

[56] References Cited

U.S. PATENT DOCUMENTS

| | | | |
|---|---|---|---|
| 2,367,690 | 1/1945 | Purdy | 128/132 |
| 3,234,941 | 2/1966 | Tucker | 128/154 |
| 4,134,399 | 1/1979 | Halderson | 128/132 |
| 4,595,011 | 6/1986 | Phillips | 128/760 |
| 4,788,971 | 12/1988 | Quisno | 128/743 |
| 4,957,108 | 9/1990 | Schoendorfer | 128/636 |

OTHER PUBLICATIONS

Toxicology and Industrial Health, vol. 3, No. 3, 1987, p. 407, lines 26–30, "Percutaneous and Oral Absorption of Chlorinated Paraffins in the Rat".

Primary Examiner—Lee S. Cohen
Assistant Examiner—J. P. Lacyk
Attorney, Agent, or Firm—Alexander J. McKillop; Charles J. Speciale; Michael J. Mlotkowski

[57] ABSTRACT

A protective cell for use in conducting dermal studies on mammals. The protective cell comprises a shell-like section terminating in a leading edge and a rim section integral to the leading edge of the shell-like section and contoured to form a surface for contacting the animal so that the area of skin to be used for the dermatological study is protected. The cavity of the shell-like section is of a shape and volume sufficient to substantially eliminate contact of the interior surface of the shell-like section with the mammal. A method for conduting dermal studies is also provided.

7 Claims, 2 Drawing Sheets

APPARATUS FOR CONDUCTING MAMMALIAN DERMATOLOGICAL STUDIES

This is a division of copending application Ser. No. 372,489, filed on Jun. 28, 1989 now U.S. Pat. No. 4,971,066.

FIELD OF THE INVENTION

The present invention relates to a method for evaluating the effects on mammals of various substances via the dermal route of administration. In particular, the present invention relates to such tests which are aided by the use of a protective, cell-type apparatus, and to such an apparatus, itself.

BACKGROUND OF THE INVENTION

In most cases, human contact with chemical substances can be characterized as being of the low-level exposure type. To predict the likelihood that such exposure may adversely impact an individual, simulative studies are performed in animals exposing them to such chemicals in nearly the same manner as humans are exposed, that is, in the diet, by inhalation, or by dermal application.

The validity of the use of data obtained from experiments with animals in providing some indication of the existence and severity of the potential hazards which humans are subjected to in certain situations depends upon correlations grounded in actual experience with those situations. The use of rodents in the estimation of the relative carcinogenic activity of various materials on human skin is broadly accepted. The general similarity of response of the skin of rodents and humans to certain known carcinogenic materials, including shale oils, spindle oils and the like, is well documented. Exemplary studies are found in: Leitch, A., "Paraffin Cancer and Its Experimental Production," *British Medical Journal*, 2:1104–6, 1922; Scott, A., "On the Occupation Cancer of the Paraffin and Oil Workers in the Scottish Shale Oil Industry," *British Medical Journal*, 2:1108–9, 1940; Twort, C. C. and Twort, J. M., "The Relative Potency of Carcinogenic Tars and Oils," *Journal of Hygiene*, 29:373–79, 1930; and, Horton, A. W. and Denman, D. T., "Carcinogenesis of the Skin. A Reexamination of Methods for the Quantitative Measurement of the Potencies of Complex Materials," *Cancer Research*, 15:701–09, 1955.

During the past seventy years, methods for evaluating systemic hazards from skin contact have been used on a large scale, and it has now become common practice to determine the toxicity of a new material by dermal application. The National Research Council has published a summary of methods for the evaluation of skin irritancy, the most common of which employ the use of small animals, such as guinea pigs, rabbits, rats and mice. See Committee on Toxicology, "Principles and Procedures for Evaluating the Toxicity of Household Substances," Pub. No. 1138, National Academy of Sciences, National Research Council, Washington, D.C., 1964.

Generally, when determining acute dermal toxicity, chemical substances are applied to the clipped skin of the animal in varying quantities and held in place for 24 hours by a sleeve of occlusive plastic sheeting or a rubber dam. Observations are made for at least two weeks. Such tests allow an estimate of the hazard of serious systemic effects by dermal contact, and they may give an idea of the rapidity of absorption. Generally they do not provide a quantitative measure of the percentage of the applied dose that has penetrated the skin. Some substances may be absorbed into the skin but not penetrate it. Quantitative data can be obtained in a variety of ways such as by tracer substances or measuring their concentration in blood or excretion in urine. Evaluations in these and other related tests often include clinical observations, weight gain, skin irritation, and blood cell and serum chemistry evaluations. At the end of a study, gross and microscopic examinations and sperm evaluations may be performed.

While occlusive sheeting and the like find utility in various chemical absorption studies, such as the aforementioned acute dermal toxicity study, other dermal assessments require the use of non-occlusive coverings for the treated area. For example, when seeking to assess the impact of low-level human chemical exposure, permitting the skin of the test animal to breathe in the usual manner enhances the simulative value of the test. While leaving the treated area of the test animal uncovered would be desirable from the standpoint of human exposure simulation, doing so often allows the animal to remove the substance in any of a variety of ways, thus impairing test integrity. For example, during grooming, the animal could potentially ingest the material and, thus, destroy the ability to assess the impact of the material through dermal absorption, alone. To aid in the small-dose study of materials having good percutaneous absorption characteristics, small, disk-like cells, such as the 1.25 centimeters diameter teflon cell available from Crown Glass Company, of Somerville, N.J., have been developed. Such cells are generally provided with an adhesive material applied to its perimeter for affixing the cell to the test animal. While these non-occlusive cells function adequately when used to study the types of materials for which they were designed to accommodate, they are inadequate in the study of materials of lower dermal penetration, such as those encountered in the study of contaminated soils.

Concern regarding dermal exposure to soils contaminated with potentially toxic materials such as dioxins, pesticides, heavy metals, polynuclear aromatics (PNA) and petroleum products containing PNA, has prompted the government and private sector to examine and formulate dermal risk assessment methodologies for contaminated soils. In the absence of experimentally determined percutaneous absorption values, many risk assessment schemes substitute available animal toxicology data on the pure contaminant, estimate dermal penetration of pure contaminant based on physicochemical models or, in the extreme, assume 100% bioavailability of the contaminant for soil (U.S. EPA 1986). Risk assessment based on these approaches is likely to result in an overestimate of dermal bioavailability of contaminants from soil, particularly for the water insoluble lipophilic compounds found in petroleum products. Therefore, toxicology data obtained using actual samples of contaminated soils are needed to provide proper risk assessment of these materials.

As mentioned, contaminated soils generally possess low dermal penetration characteristics. As such, they must be applied to a larger portion of the dorsal area of the animal to properly assess the risk of exposure to such a material. While many pure substances may be adequately tested by applying them to as little as one square centimeter of the dorsal area of an animal, to test substances of poor dermal penetration, such as contaminated soils, areas in excess of five square centimeters must often be treated. Because of the necessity to treat a relatively large area of the animal's dorsal region, the presently known non-occlusive cells are clearly inadequate. Merely fabricating a larger flat, disk-like, non-occlusive cell would not be satisfactory since, as the animal moves about, its skin-layer would move to an extent sufficient to cause contact with such a larger disk-like cell. This contact of the treated dorsal area with the surface of the cell would substantially impair the integrity of the evaluation. Also, there exists a practical difficulty when attempting to attach a disk-like cell to the dorsal area of an animal, particularly when using a flat cell having a cross-sectional area of at least 5 cm$^2$. This is due to the fact that proper adhesion of such a cell to the dorsal skin cannot be achieved over the entire contact area.

Therefore, what is needed is a cell capable of protecting an area of skin large enough to permit the testing of materials having lower dermal penetration characteristics without permitting the contact of treated skin with the cell.

SUMMARY OF THE INVENTION

According to the present invention, there is provided a protective cell for conducting mammalian dermatological studies which comprises a shell-like section, terminating in a leading edge, having interior and exterior surfaces, a rim section integral to the leading edge of the shell-like section, the rim section contoured to form a surface for contacting the mammal so that the area of skin to be used for the dermatological study is protected. The cavity of the shell-like section is of a shape and volume sufficient to substantially eliminate contact of the interior surface of the shell-like section with the area of skin which is to be used for the dermal study when the mammal moves about in its daily activities.

It is an object of the present invention to provide a cell capable of protecting an area of skin to be used in a mammalian dermal study which is of a size which enables the testing of materials of lower dermal penetration characteristics without permitting contact of the skin used for the study with the interior surface of the cell.

It is another object of the present invention to provide a protective cell for mammalian dermal studies which is non-occlusive.

It is a further object of the present invention to provide a protective cell for mammalian dermal studies which is contoured to adapt to the dorsal area of the mammal to enhance the protective nature of the cell.

It is yet another object of the present invention to provide a protective cell for use in mammalian dermal studies which is chemically inert relative to the substances to be tested.

It is yet a further object of the present invention to provide a method of conducting a mammalian dermal study utilizing a non-occlusive protective cell adapted for the testing of substances of lower dermal penetration characteristics.

Other objects, aspects and the several advantages of the present invention will become apparent to those skilled in the art upon a reading of the specification and the claims appended thereto.

BRIEF DESCRIPTION OF THE DRAWINGS

FIG. 2 shows the protective cell from several views for completeness.

DESCRIPTION OF THE PREFERRED EMBODIMENTS

The present invention relates generally to a protective device for use in evaluating the effects on mammals of various substances administered via the dermal route. Such substances may include chemicals, hydrocarbon products and contaminated soils. Also, the present invention embraces a method for conducting such a test. The invention is particularly suited to dermal studies conducted over a relatively large cross-sectional area of mammalian skin.

As previously discussed, existing methods and protective cells are inadequate when testing substances having lower percutaneous absorption characteristics. This is due primarily to the fact that such substances must be applied to a larger area of the animal's skin for proper evaluation. Existing disk-like protective cells are too small to find utility in these applications and merely enlarging such a cell produces a device which will cause contact of the cell with the treated skin and possible removal of the substance to be evaluated through contact with the interior surface of such a cell.

The present invention overcomes the problems previously encountered by providing a protective cell of a size and shape which enhances the ability of the investigator to perform valid dermal studies of substances having lower percutaneous absorption characteristics. The protective cell and test method disclosed herein can be used on any small animal, with guinea pigs, rabbits and rats preferred. Of the aforementioned mammals, rats are particularly preferred.

Figure 1:
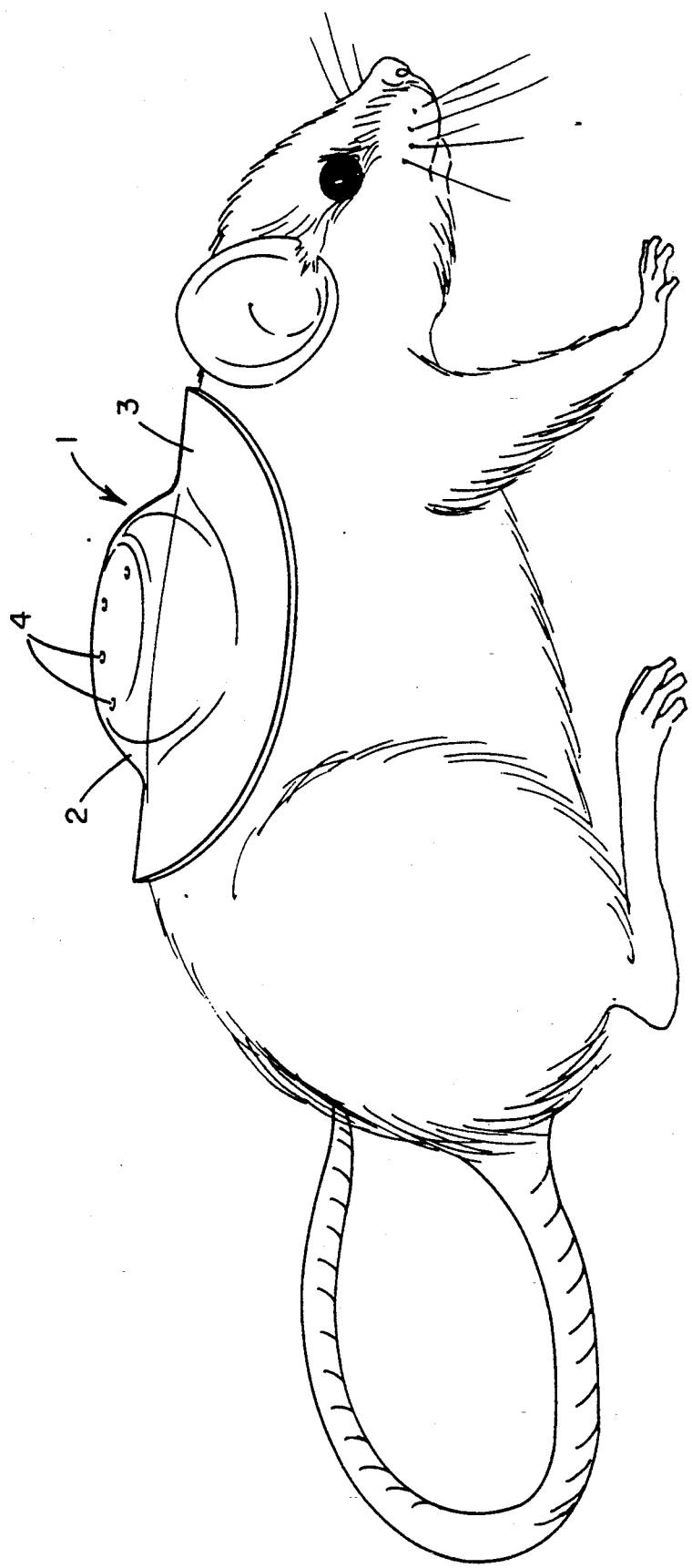
FIG. 1 shows a protective cell, according to the present invention, in place and covering the dorsal region of a rat.
Figure 2A:
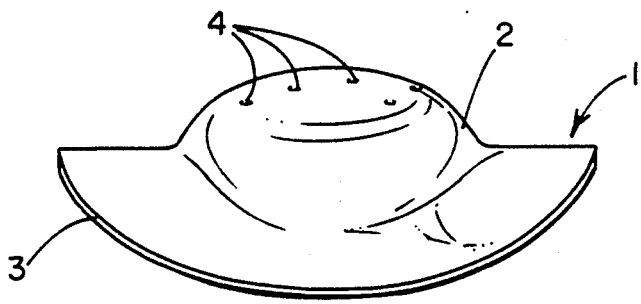
FIG. 2A is a side view of the protective cell according to the present invention.
Figure 2B:
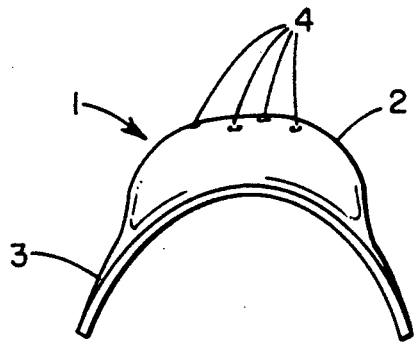
FIG. 2B is an end view of the protective cell.
Figure 2C:
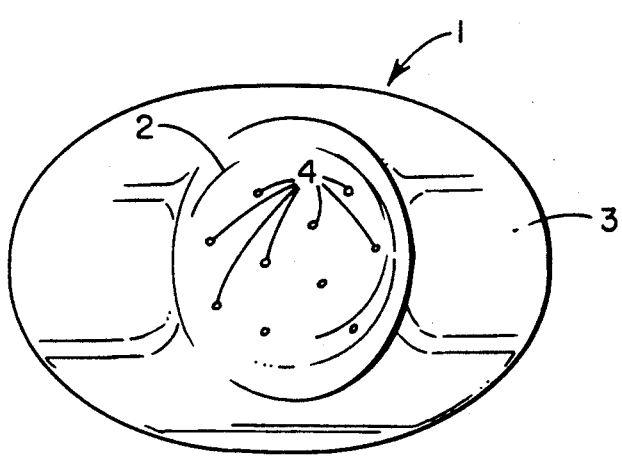
FIG. 2C is a top view of the protective cell.
Figure 2D:
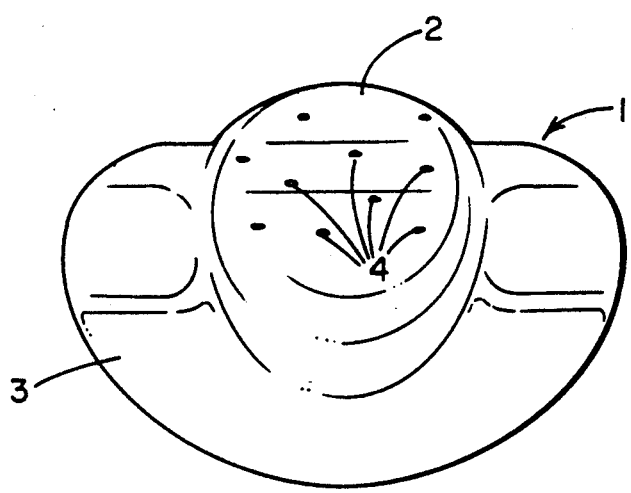
FIG. 2D is a view in perspective of the protective cell.

As shown in FIG. 1, which as with all figures presented herein is given by way of example and illustration and not of limitation, the protective cell 1 of the present invention may be used advantageously to protect the dorsal area of the animal and is shaped especially for that purpose. The dorsal area is particularly preferred for dermal testing since it is the most difficult area for the animal to disturb and provides a good surface for the investigator to perform his study, relative to other parts of the animal's body.

The protective cell 1 has a shell-like section 2 which defines a cavity formed by its inner surface. This cavity is of a shape and volume sufficient to substantially eliminate contact of the interior surface of the shell-like section 2 with the dermal test area. In studies of the movement of rats and particularly their skin during such tests, it has now been found that a clearance of at least about 1.0 centimeter is required between the dorsal skin surface of the animal and the inner surface of the protective cell in order to substantially eliminate result-impairing contact. The animals so studied were the well-known Sprague-Dawley rats of three to six months of age. A clearance of at least about 1.5 centimeters between these surfaces is particularly preferred for these tests.

Integral to the leading edge of shell-like section 2 of protective cell 1 is rim section 3. As may be seen, rim section 3 is advantageously shaped to approximate the contour of the dorsal area of the test animal. This contour permits close contact with the animal, prohibiting the entry of foreign matter or objects onto the test skin site and, additionally, precludes the animal from contacting the area during grooming. This feature is of particular concern when seeking to eliminate other sources of possible test substance administration, as it is apparant that, during grooming, the animal can inadvertently self-administer the substance orally, as those skilled in the art will readily recognize. Overall, the preferred shape of the rim section 3 is elliptical, rather than circular, being dimensionally longer in the animal's spinal direction than transversely to same. This preferred elongated shape provides substantial means for securing the cell 1 to the animal.

Cell 1 may be secured to the test animal with a suitable adhesive (not shown), with an epoxy adhesive being particularly preferred. Additionally, if desired, the cell may be further secured by wrapping a suitable tape (not shown) around the elongated ends of the protective cell 1 and the animal.

While the cell may be of multi-piece construction, it is preferred that it be formed from a single piece of material. Further, it is preferred, as those skilled in the art will plainly recognize, that the material selected for forming the cell be chemically inert vis-a-vis the substances selected for evaluation. In this regard, glass and teflon are preferred materials. Additionally, the cell can be constructed from non-inert materials and subsequently coated with a chemically inert material to obtain the desired characteristics. The cells may be formed by thermoforming, injection molding, glass blowing or any well-known technique for making similar structures.

The cells may be fabricated to be substantially occlusive or non-occlusive depending upon the testing goals of the individual investigator. When a non-occlusive cell is desired, holes 4 may be added to shell-like section 2 of cell 1. It has been found that about 8 to 15 holes of approximately 0.02 inches in diameter are sufficient to achieve the desired non-occlusive effect in cells designed to cover dermal test areas of about seven square centimeters (about three centimeters in diameter). Holes 4 may be drilled or molded into the cell structure or produced in any well-known technique.

Reference is now made to FIGS. 2-A through 2-D. In sizing the protective cell of the present invention, it is preferred that the shell-like section 2 at least enclose the dermal test area to be treated. For example, if a circular area of seven square centimeters is to be subjected to skin-painting study, then the shell-like section should be at least about three centimeters in diameter. Although FIG. 2-C shows a protective cell 1 having a shell-like section 2 which is substantially circular, other shapes and forms are useful in dermal studies as those skilled in the art will plainly recognize. For example, a substantially rectangular or elliptical cell would be expected to have utility and is deemed to be within the scope of the present invention.

Any dermatological study conducted on small animals which requires that the treated area be protected is contemplated herein. Methods such as those disclosed by Yang, J. J., Roy, T. A., Neil, W., Krueger, A. J. and Mackerer, C. R. in the paper entitled "Percutaneous and Oral Absorption of Chlorinated Paraffins in the Rat," *Toxicology and Industrial Health*, 3:405–411, 1987, and by Yang, J. J., Roy, T. A., Krueger, A. J., Neil, W. and Mackerer, C. R. in the paper entitled "In Vitro and In Vivo Percutaneous Absorption of Benzo [a] pyrene from Petroleum Crude-Fortified Soil in the Rat," *Bulletin of Environmental Contamination and Toxicology*, 43: Aug., 1989, are exemplary. These references are incorporated herein for the methodology that they disclose.

The following non-limiting example is illustrative of the present invention.

EXAMPLE

Male and female Sprague-Dawley rats (obtained from Charles River Laboratories, Lakeview, N.Y.), 3–6 months old, were housed in wire mesh cages prior to treatment. Animal rooms were maintained at 70° F. and 50% relative humidity with a 12-hour light-dark cycle. Food (Lab Chows, obtained from Ralston Purina Company, St. Louis, M.O.) and water were provided ad libitum. The animals were divided into treatment groups of five to seven rats per sex and individually housed in metabolic cages.

For these experiments, the dorsal area of each rat was lightly shaved after mild anesthesia. Appropriate amounts of crude alone or 1% crude-fortified soil containing $^3$H-radiolabelled surrogate were applied over a 7 cm$^2$ skin surface area. The dosed area was covered with a non-occlusive glass cell of the present invention. The cell was attached to the skin with an epoxy adhesive and further secured with tape. The dosed animals were individually housed in Nalgene metabolism cages and offered food and water ad libitum. Urine and feces were collected once daily for four days. During this four day study, each rat was visually inspected to insure that the protective cell had not contacted the treated dorsal area of the rat and that the cell was still firmly affixed. Despite the freedom of each rat to move about its cage more or less undisturbed by the protective cell, no evidence of contact was observed and all cells remained firmly affixed. Additionally, as evidenced by the coloration and overall appearance of the skin, the cells were found to be suitably non-occlusive. (Each cell used for this study had 10 randomly-spaced holes of approximately 0.02 inches in diameter drilled through the shell-like sections.)

At the termination of the experiment, samples of liver, kidney, small and large intestine, stomach, bladder and blood were collected from each animal. Radioactivity in the urine, feces, blood and tissue samples was determined by counting in a Beckman LS 9000 liquid scintillation counter (Fullerton, CA). The radioactivity in the urine samples was measured directly after addition of scintillation fluid. Fecal and most tissue samples were homogenized and combusted in a Harvey OX300 biological oxidizer (obtained from Harvey Corporation of Hillsdale, NJ) before being counted. However, samples of urinary bladder, muscle, bone, gonads, fat and blood were combusted without prior homogenization.

Although the present invention has been described with preferred embodiments, it is to be understood that modifications and variations may be utilized without departing from the spirit and scope of this invention, as those skilled in the art will readily understand. Such modifications and variations are considered to be within the purview and scope of the appended claims.

What is claimed is:

1. A substantially chemically inert protective cell for conducting mammalian dermatological studies of chemically contaminated soil, consisting essentially of:
   (a) a non-occlusive shell-like section terminating in a leading edge said shell-like section having an interior and an exterior surface, said shell-like section defining a cavity of a shape and volume sufficient to substantially eliminate contact of said interior surface of said shell-like section with the area of skin used for the dermatological study when the mammal moves about; and
   (b) an elliptical rim section contoured to form a surface for contacting a mammal's dorsal region and surrounding an area of skin for use in the dermatological study said rim section integral to said leading edge of said shell-section;
   wherein said shell-like section and said rim section are formed from a single piece of material which is chemically inert in relation to the chemically contaminated soil.

2. The protective cell of claim 1, wherein said shell-like section has a planar cross-sectional area at least equal to the dermal test area of the mammal.

3. The protective cell of claim 2, wherein said planar cross-sectional area of said shell-like section is at least about five square centimeters.

4. The protective cell of claim 3, wherein said planar cross-sectional area is about seven square centimeters.

5. The protective cell of claim 1, wherein said non-occlusive shell-like section includes a plurality of holes of sufficient size and number to permit dermal transpiration.

6. The protective cell of claim 1, which is formed from glass.

7. The protective cell of claim 6, wherein said rim section is contoured for contacting the dorsal region of a rat.

* * * * *